US012427235B2

(12) United States Patent
Zacharia et al.

(10) Patent No.: US 12,427,235 B2
(45) Date of Patent: Sep. 30, 2025

(54) COMBINED EXTRACORPOREAL AND DRUG DELIVERY SYSTEM AND METHOD (71) Applicants: BAXTER INTERNATIONAL INC., Deerfield, IL (US); BAXTER HEALTHCARE SA, Glattpark (CH)

(72) Inventors: John Ramez Zacharia, Chicago, IL (US); Bernd Wittner, Minneapolis, MN (US); Matthew Bivans, Barrington, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 292 days.

(21) Appl. No.: 17/116,561

(22) Filed: Dec. 9, 2020

(65) Prior Publication Data
US 2021/0170084 A1 Jun. 10, 2021

Related U.S. Application Data (60) Provisional application No. 62/946,205, filed on Dec. 10, 2019.

(51) Int. Cl.
A61M 1/16 (2006.01)
A61M 1/30 (2006.01)
(Continued)

(52) U.S. Cl.
CPC .......... A61M 1/1615 (2014.02); A61M 1/308 (2014.02); A61M 1/3607 (2014.02);
(Continued)

(58) Field of Classification Search
CPC ............... A61M 1/1615; G16H 20/40
See application file for complete search history.

(56) References Cited

U.S. PATENT DOCUMENTS 6,325,774 B1 * 12/2001 Bene .................... A61M 1/1609
604/4.01
2005/0085760 A1 * 4/2005 Ware .................... A61M 1/3437
604/4.01
(Continued)

FOREIGN PATENT DOCUMENTS

EP 2380609 A1 * 10/2011 ............. A61M 1/16

OTHER PUBLICATIONS

Decker, Brian S., Bruce A. Mueller, and Kevin M. Sowinski. "Drug dosing considerations in alternative hemodialysis." Advances in chronic kidney disease 14.3 (2007): e17-e26. (Year: 2007).*

(Continued)

Primary Examiner — Bradley R Spies
Assistant Examiner — Jeannie McDermott
(74) Attorney, Agent, or Firm — K&L Gates LLP (57) ABSTRACT An extracorporeal and drug delivery system includes (i) a renal failure therapy machine operable with a blood filter in fluid communication with an arterial line and a venous line, the machine including (a) an effluent pump for pumping effluent from the blood filter at an effluent flowrate, and at least one of (b) a dialysis fluid pump for pumping dialysis fluid to the blood filter at a dialysis fluid flowrate, (c) a predilution pump for pumping replacement fluid into the arterial line at a predilution flowrate, or (d) a postdilution pump for pumping replacement fluid into the venous line at a postdilution flowrate; (ii) an infusion pump operable to deliver an intravenous ("IV") drug to the patient at an IV drug flowrate; and (iii) a coordinating logic implementor configured to adjust the IV drug flowrate based on an amount of the IV drug removed via the effluent flowrate.

21 Claims, 4 Drawing Sheets (51) Int. Cl.
*A61M 1/36* (2006.01)
*A61M 1/38* (2006.01)
*A61M 5/168* (2006.01)

(52) U.S. Cl.
CPC ............ *A61M 1/3621* (2013.01); *A61M 1/38* (2013.01); *A61M 5/168*77 (2013.01); *A61M 2205/3553* (2013.01)

(56) References Cited

U.S. PATENT DOCUMENTS

| | | | | |
|---|---|---|---|---|
| 2009/0221948 | A1* | 9/2009 | Szamosfalvi | A61M 1/3441 604/6.07 |
| 2011/0168614 | A1* | 7/2011 | Pouchoulin | A61M 1/3434 210/134 |
| 2013/0248426 | A1* | 9/2013 | Pouchoulin | A61M 1/1643 210/96.2 |
| 2014/0074008 | A1* | 3/2014 | Fontanazzi | A61M 1/1605 604/5.04 |
| 2015/0343129 | A1* | 12/2015 | Surace | A61M 1/341 604/6.09 |
| 2017/0043089 | A1* | 2/2017 | Handler | G16H 20/40 |
| 2019/0217002 | A1* | 7/2019 | Urakabe | A61M 1/367 |
| 2020/0368418 | A1* | 11/2020 | Yuds | A61M 1/3607 |
| 2021/0379262 | A1* | 12/2021 | Lerner | A61M 1/3441 |

OTHER PUBLICATIONS

Gary R. Matzke, et.al, Drug dosing consideration in patients with acute and chronic kidney disease—a clinical update from Kidney Disease: Improving Global Outcomes (KDIGO), Kidney International, vol. 80, Issue 11, 2011, pp. 1122-1137, ISSN 0085-2538, https://doi.org/10.1038/ki.2011.322. (Year: 2011).*

* cited by examiner

COMBINED EXTRACORPOREAL AND DRUG DELIVERY SYSTEM AND METHOD

PRIORITY CLAIM

This application claims priority to and the benefit of U.S. Provisional Application No. 62/946,205, filed Dec. 10, 2019, entitled "Combined Extracorporeal and Drug Delivery System and Method", the entire contents of which are incorporated herein by reference and relied upon.

BACKGROUND

Acute kidney injury ("AKI") is more common than most people know and is under-recognized in hospital patients, especially in certain countries. It has been reported that worldwide, twenty percent of hospitalized patients have AKI. A larger number of intensive care unit ("ICU") patients have AKI, where fifteen to twenty-five percent of such patients receive some form of renal replacement therapy ("RRT"). Approximately twenty-seven percent of pediatric and young adult ICU patients develop AKI during the first week after admission to the hospital.

Major contributors to AKI include septic shock (~47% of instances), major surgery (~34% of instances), cardiogenic shock (~27% of instances), hypovolaemia (~25% of instances), drug induced (~19% of instances), hepatorenal syndrome (~6% of instances) and obstructive uropathy (~3% of instances).

RRT for patients with AKI includes both intermittent hemodialysis ("IHD") and continuous renal replacement therapy ("CRRT"). IHD may treat the patient over three to four hours every other day for example. CRRT instead treats the patient continuously using much slower blood and treatment fluid flowrates. Certain studies have shown that CRRT is preferable to IHD for treating AKI. For example, fluid accumulation after a few days in the hospital may be lower for patients receiving CRRT versus IHD. Additionally, CRRT may be preferable to IHD regarding the frequency of patients ultimately developing chronic kidney disease ("CKD"), i.e., less patients treated with CRRT develop CKD versus patients treated with IHD.

CRRT is performed using a CRRT machine. CRRT machines perform different types of CRRT therapies, for example, slow continuous ultrafiltration ("SCUF") for fluid removal only, continuous veno-venous hemodialysis ("CVVHD"), continuous veno-venous hemodiafiltration ("CVVHDF"), and continuous veno-venous hemofiltration ("CVVH"). CRRT machines may perform other types of therapies, such as therapeutic plasma exchange ("TPE"), which typically involves plasmafilters and multiple indications, such as for auto-immune diseases, hemoperfusion involving adsorption devices, MARS therapy for liver support, and extracorporeal $CO_2$ removal ("ECCO2R"), such as for lung support using an oxygenator. CRRT machines also allow for different types of anticoagulation modalities, such as systemic anticoagulation (e.g., heparin) and regional citrate anticoagulation ("RCA").

Hospitalized patients with AKI often require a multitude of drugs to treat other ailments, which are delivered at precise intervals and concentrations to ensure proper recovery. Such patients are therefore simultaneously connected to a CRRT or IHD machine. Both machines remove blood from the patient, run the blood through a filter to remove solutes, thereby upsetting the concentrations or pharmokinetics of other therapies, drugs, or solutions being applied to the patient during the same hospital stay.

To compensate for the effects of the essential extracorporeal therapies, physicians have to manually calculate changes as one therapy is added or changed, resulting potentially in underdelivery or overdelivery of medications and risk to the patient. An improved overall regime for treating hospitalized patients with AKI is needed accordingly.

SUMMARY

The present disclosure sets forth a combined extracorporeal and drug delivery system and method, which provides a coordinating logic implementor that coordinates operation of a CRRT machine or an IHD machine (e.g., chronic-type hemodialysis machine) with one or more infusion pump simultaneously delivering a drug to the same patient. The synchronized operation may include: (i) electronically and/or data connecting to all infusion and extracoporeal devices treating the patient, (ii) registering treatment settings, including blood flow rates, treatment fluid flow rates, fluid removal rates, drug types and doses for the drugs, (iii) providing decision support to a prescribing physician regarding drugs to apply and target doses, which follow commonly accepted literature guidance and consider patient characteristics, disease type, and state, (iv) calculating actual dosing to reach desired dosing, and making adjustments as necessary to maintain the desired dose over time, (v) causing the flowrate or adjustment information to be communicated to the operator for approval or transmit the information to the connected infusion and extracoporeal devices to automatically make the adjustments for administering the drug and/or treatment fluid to the patient, and (vi) optionally synchronizing with associated hospital IT systems such as an electronic medical record database, medical monitoring, telemedicine, or operational platforms, to report the treatment data and other data, such as treatment results, types and doses of drugs delivered, caregiver notes, e.g., patient subjective feelings, presence of septic or infectious conditions, and the like. Decision support for target doses, for example, may includes an indication of risk and a probability of future state of the patient, e.g., regarding blood pressure changes, fluid overload, and/or cardiac issues. In this manner, the synchronized operation may bring value over and above coordination between renal failure and infusion pump operation.

The intravenous ("IV") drugs delivered during the CRRT or IHD treatment may include any type of antibiotic, such as vancomycin, gentamicin, cefepime, piperacillin, tazobactim, ceftazidime, avibactam, cefazolin, aztreozam, nafcillin, oxacillin. Other drugs include meropenem, cefepime, and fluconazole. Other drugs in which dosing is challenged by renal failure treatment and thus benefit from being synchronized with renal failure flowrates according to the present disclosure include any type of fluid resuscitation drug, systemic anticoagulation drug, e.g., heparin or citrate, vasopressors, electrolytes, trace elements, nutritional supplements, anticonvulsants, antifungals, antineoplastic, neuromuscular blocking, analgesic, and/or immunosupressent. Any drug that may be administered in combination with a CRRT or IHD treatment is contemplated for the present system and method.

It is desirable for a coordinating logic implementor of the present disclosure to be able to operate with existing CRRT machines, IHD machines and infusion pumps (including but not limited to large volume infusion pumps ("LVP"), syringe pumps, bladder pumps, drip pumps and any other type of IV drug pump), so that in one embodiment, the coordinating logic implementor is located externally to each of the machines, e.g., resting on, connected to or located adjacent to the CRRT or DID machine. In one preferred embodiment, the coordinating logic implementor is in electronic and/or data communication with the CRRT or DID machine, e.g., via a wired or wireless connection. In an alternative embodiment, the coordinating logic implementor may be provided as a portion of the overall control unit of the CRRT or IHD machine and thus be located within same.

In various embodiments, the coordinating logic implementor may or may not be in electronic and/or data communication with the one or more infusion pump, for example, depending on the communication capability of the pump. It may be that the coordinating logic implementor is able to communicate wired or wirelessly with all of the infusion pumps, some of the infusion pumps, or none of the infusion pumps. If the infusion pumps are connected to the coordinating logic implementor, then they may be controlled automatically or upon confirmation and setting by the operator. If the infusion pumps are not connected to the coordinating logic implementor, then they may be controlled manually upon confirmation and setting by the operator who may view the recommendation either at a display screen of the coordinating logic implementor or of the CRRT or IHD machine.

The coordinating logic implementor coordinates the operation of the CRRT or IHD machine and the infusion pumps in multiple ways. One way is for the system to take into account the flowrates of the IV drugs in the prescribed fluid removal or ultrafiltration calculation. A goal of a CRRT or IHD treatment may be to remove fluid from the patient so that the patient who is experiencing AKI does not gain fluid over time. An IV drug may contribute in a significant way to the overall amount of fluid delivered to the patient. The IV delivery amount is taken into consideration in determining an instantaneous effluent flowrate removed by the CRRT or IHD machine. The coordinating logic implementor also knows when the IV drug is being delivered, such that it may command a higher effluent flowrate during drug delivery and a lower effluent flowrate when drug delivery is halted. The coordinating logic implementor repeats this analysis for each IV drug being delivered during the CRRT or IHD treatment and combines the results when two or more drug deliveries overlap.

Another way in which coordinating logic implementor coordinates the operation of the CRRT or IHD machine and the infusion pumps is to adjust one or more infusion pump administration rate to compensate for a portion of the drug intended for the patient instead being removed from the extracapoeral circuit as effluient via the CRRT or IHD treatment. In an embodiment, an estimation is made as to the percentage of the drug within the effluent removed. The estimation may be made using one or more assumption, such as, the effluent being fully hemogoneous and the estimation of the patient's blood volume, which may be esitmated based on the patient's weight. In an alternative embodiment, the patient's blood volume may be determined prior to treatment and entered into coordinating logic implementor, e.g., via a user interface associated with the coordinating logic implementor or via the user interface the CRRT or IHD machine, which in turn relays the blood volume wired or wirlessly to the coordinating logic implementor.

If the estimated drug percentage is, for example, one percent, then the coordinating logic implementor may either increase the flowrate associated with the prescribed drug by one percent or recommend to the operator a flowrate setpoint that is one percent higher than the flowrate associated with the prescribed dosage. The increased IV drug flowrate, if automatically implemented or if accepted by the operator, may be taken into account in the effluent flowrate adjustment discussed above or ignored if it would have a negligable inpact. Raising the IV drug flowrate in this manner compensates for the amount of IV drug removed via effluent removal of the CRRT or IHD machine.

In determining whether to adjust the flowrate for an IV drug, the coordinating logic implementor may take into account whether the CRRT or IHD machine is actually running. For example, if the IV drug is delivered before or after CRRT or IHD treatment, the coordinating logic implementor does not adjust the IV drug flowrate from the flowrate associated with the prescribed dosage. If the CRRT or IHD machine is stopped for watever reason during treatment, e.g., due to an alarm, alert, supply bag change, etc., the coordinating logic implementor is informed of the stoppage and may react in a plurality of alternative ways, for example, (i) automatically reduce or suggest to reduce the IV drug flowrate to the flowrate associated with the prescribed dosage while the stoppage persists, (ii) maintain the IV drug flowrate at the elevated flowrate during the stoppage but count the additional flowrate as being part of the administered dosage, so that overall drug delivery time may be reduced to meet the prescribed dosage, or (iii) shut down the IV drug flowrate completely, e.g., if the drug is meant to accompany the CRRT or IHD treatment, e.g., if the drug is an anticoagulant, phosphorous supplement, and the like.

Alternatively or in addition to adjusting IV pump flowrate (s) so that an actual IV dose received by a patient meets a prescribed dose for the patient despite IV drug lost due to effluent removal from a renal failure therapy, it is also contemplated that the present system and method adjust IV drug concentration. For example, the acutal concentration of one or more IV drug may be increased from a prescribed concentration so that the actual amount of the drug absorbed by the patient meets an expected prescribed amount of drug absorbed by the patient taking into account an amount of drug lost via effluent removal.

It is contemplated for the present system and method to compensate (e.g., decrease) the increase in IV drug flowrate or concentration due to a clotting of the blood filter over time, which may lessen the amount of IV drug removal for a set effleunt removal flowrate. The amount of clotting may be estimated by a pressure increase, e.g., effluent line pressure increase, which is correlated in a lookup table, e.g., empirically, with varying amounts of IV drug removal decrease. The system of the present disclosure receives the increasing pressure signals over the course of treatment, invokes the lookup table and adjusts (e.g., decreases) the percentage increase in IV drug flowrate and/or concentration accordingly.

Further alternatively, IV fluid flowrate or concentration may be adjusted based on an amount of dilution due to replacement fluid flow and/or dialysis fluid flow as opposed to effluent fluid flowrate. Here, the adjustment may be based on a relationship between the flowrates of the IV fluid, replacement fluid flow and/or dialysis fluid.

In another aspect of the system and method of the resent disclosure, the chemical constituency of the IV fluid, replacement fluids and/or dialysis fluid are analyzed and overlapping chemicals or constituents are compared to allowable levels to see if the chemical makeup of the IV fluid should be adjusted or if the combined chemical or constituent dose is acceptable. If it is determined that the IV drug constituency needs to be modified, the present system outputs a revised formulation for approval and subsequent compounding at the hospital's pharmacy, for example.

At the end of, or at any suitable time throughout, the CRRT or IHD treatment and drug delivery, it is contemplated to send any or all relevant treatment data to an electronic medical record ("EMR") database of the hospital, which stores a file for the patient. To do so, it is contemplated for the coordinating logic implementor to be in wired or wireless communication with a hospital server or other computer storage for the EMR database, data warehouse or data lake.

In a typical hospital or emergency room setting, it is likely that there will only be one CRRT or IHD machine and associated one or more infusion pump. In such a case, there will be a dedicated coordinating logic implementor for the arrangment of machines, which acts as a hub to the spoke medical machines. In a more clinical setting, e.g., using hemodialysis machines for IHD, where IV drug delivery may still take place, it is contemplated to provide a coordinating logic implementor that is dedicated to two or more CRRT or IHD machines and associated infusion pump. Here, the coordinating logic implementor may (i) again be the hub to all of the spoke medical machines, including the CRRT or IHD machines, or (ii) be a higher level hub to each of the spoke CRRT or IHD machines in its cluster, wherein the CRRT or IHD machines are in turn lower lever hubs to their associated spoke infusion pumps. The latter arrangment may be preferred when shorter range wireless communication is provided.

In light of the disclosure herein, and without limiting the scope of the invention in any way, in a first aspect of the present disclosure, which may be combined with any other aspect listed herein, or portion thereof, an extracorporeal and drug delivery system including (i) a renal failure therapy machine operable with a blood filter in fluid communication with an arterial line for removing blood from a patient to the blood filter and a venous line for returning blood from the filter to the patient, the renal failure therapy machine including (a) an effluent pump positioned and arranged to pump effluent from the blood filter at an effluent flowrate, and (b) at least one of a dialysis fluid pump positioned and arranged to pump dialysis fluid to the blood filter at a dialysis fluid flowrate, a predilution pump positioned and arranged to pump replacement fluid into the arterial line at a predilution flowrate, or a postdilution pump positioned and arranged to pump replacement fluid into the venous line at a postdilution flowrate; (ii) an infusion pump operable to deliver an intravenous ("IV") drug to the patient at an IV drug flowrate; and (iii) a coordinating logic implementor configured to determine an adjustment for the IV drug flowrate based on an amount of the IV drug removed via the effluent flowrate.

In a second aspect of the present disclosure, which may be combined with any other aspect listed herein, or portion thereof, the renal failure therapy machine is a continuous renal replacement machine, and which includes the effluent pump and at least two of the dialysis fluid pump, the predilution pump or the postdilution pump.

In a third aspect of the present disclosure, which may be combined with any other aspect listed herein, or portion thereof, the renal failure therapy machine is a hemodialysis machine, and which includes the effluent pump and the dialysis fluid pump.

In a fourth aspect of the present disclosure, which may be combined with any other aspect listed herein, or portion thereof, the coordinating logic implementor is provided separately from the renal failure therapy machine and the infusion pump, and wheren the coordinating logic implementor is in wired or wireless communication with at least the renal failure therapy machine.

In a fifth aspect of the present disclosure, which may be combined with the fourth aspect in combination with any other aspect listed herein, or portion thereof, the system is configured such that a total patient fluid input is communicated to or determined by the coordinating logic implementor for the coordinating logic implementor to determine the adjustment for the IV drug flowrate based on the amount of the IV drug removed via the effluent flowrate.

In a sixth aspect of the present disclosure, which may be combined with any other aspect listed herein, or portion thereof, the system is configured to at least one of (i) automatically implement the adjustment for the IV drug flowrate at the infusion pump or (ii) display the adjustment at one or more of the renal failure therapy machine, the infusion pump, or the coordinating logic implementor for implementation.

In a seventh aspect of the present disclosure, which may be combined with any other aspect listed herein, or portion thereof, the coordinating logic implementor is integrated into the renal failure therapy machine.

In an eighth aspect of the present disclosure, which may be combined with any other aspect listed herein, or portion thereof, wherein the infusion pump is a first infusion pump, the IV drug is a first IV drug, the IV drug flowrate is a first IV drug flowrate, which includes a second infusion pump operable to deliver a second IV drug to the patient at a second IV drug flowrate, and wherein the coordinating logic implementor is configured to determine an adjustment for the second IV drug flowrate based on an amount of the second IV drug removed via the effluent flowrate.

In a ninth aspect of the present disclosure, which may be combined with any other aspect listed herein, or portion thereof, the system is configured such that the effluent flowrate may take into account the adjustment for IV drug flowrate and at least one of the dialysis fluid flowrate, predilution flowrate, or postdilution flowrate.

In a tenth aspect of the present disclosure, which may be combined with any other aspect listed herein, or portion thereof, the system is configured such that the effluent flowrate takes into account a prescribed patient fluid loss rate.

In an eleventh aspect of the present disclosure, which may be combined with any other aspect listed herein, or portion thereof, the amount of the IV drug removed via the effluent flowrate includes a percentage of the IV drug in the effluent flowrate.

In a twelfth aspect of the present disclosure, which may be combined with any other aspect listed herein, or portion thereof, the coordinating logic implementor is configured to determine the adjustment for the IV drug flowrate based on the amount of the IV drug removed via the effluent flowrate and upon an estimation of a blood volume of the patient.

In a thirteenth aspect of the present disclosure, which may be combined with any other aspect listed herein, or portion thereof, the coordinating logic implementor is further configured to take into account blood filter patency or clotting in determining the adjustment for the IV drug flowrate.

In a fourteenth aspect of the present disclosure, which may be combined with the thirteenth aspect in combination with any other aspect listed herein, or portion thereof, the system is configured such that the adjustment causes the IV drug flowrate to meet the prescribed IV drug flowrate when the amount of the IV drug is removed via the effluent flowrate.

In a fifteenth aspect of the present disclosure, which may be combined with any other aspect listed herein, or portion thereof, the renal failure therapy machine is a first renal failure therapy machine, the infusion pump is a first infusion pump, which includes a second renal failure therapy machine associated with a second infusion pump, and wherein the coordinating logic implementor is configured to determine an adjustment for the IV drug flowrate of the second infusion pump.

In a sixteenth aspect of the present disclosure, which may be combined with any other aspect listed herein, or portion thereof, the coordinating logic implementor is alternatively or additionaly configured to determine an adjustment to a concentration of the IV drug based on an amount of the IV drug removed via the effluent flowrate.

In a seventeenth aspect of the present disclosure, which may be combined with the sixteenth aspect in combination with any other aspect listed herein, or portion thereof, the system is configured to display the concentration adjustment at one or more of the renal failure therapy machine, the infusion pump, or the coordinating logic implementor for implementation.

In an eighteenth aspect of the present disclosure, which may be combined with the sixteenth aspect in combination with any other aspect listed herein, or portion thereof, the system is configured such that the concentration adjustment causes an IV drug dose received by the patient to meet a prescribed IV drug dose when the amount of the IV drug is removed via the effluent flowrate.

In a nineteenth aspect of the present disclosure, which may be combined with the sixteenth aspect in combination with any other aspect listed herein, or portion thereof, the infusion pump is a first infusion pump, the IV drug is a first IV drug, which includes a second infusion pump operable to deliver a second IV drug to the patient, and wherein the coordinating logic implementor is configured to determine an adjustment to a concentration of the second IV drug based on an amount of the second IV drug removed via the effluent flowrate.

In a twentieth aspect of the present disclosure, which may be combined with any other aspect listed herein, or portion thereof, the coordinating logic implementor is alternatively or additionaly configured to determine an adjustment to a flowrate and/or concentration of the IV drug based on an amount of dilution of the IV drug due to at least one of the dialysis fluid flowrate, the predilution flowrate or the postdilution flowrate.

In a twenty-first aspect of the present disclosure, which may be combined with the twentieth aspect in combination with any other aspect listed herein, or portion thereof, the amount of dilution is based on a relationship between a flowrate of the IV drug and at least one of the dialysis fluid flowrate, the predilution flowrate or the postdilution flowrate.

In a twenty-second aspect of the present disclosure, which may be combined with any other aspect listed herein, or portion thereof, the coordinating logic implementor is alternatively or additionaly configured to determine if a constituent of the IV drug exists in at least one of the dialysis fluid, predilution replacement fluid or postdilution replacement fluid, and if so, determine if a formulation adjustment should be made to the IV drug.

In a twenty-third aspect of the present disclosure, which may be combined with the twenty-second aspect in combination with any other aspect listed herein, or portion thereof, the formulation adjustment includes decreasing or eliminating the constituent in or from the IV drug.

In a twenty-fourth aspect of the present disclosure, any of the structure, functionality and alternatives associated with any of FIGS. 1 to 4 may be combined with any of the structure, functionality and alternatives associated with any other of FIGS. 1 to 4.

In light of the present disclosure and the above aspects, it is therefore an advantage of the present disclosure to provide a combined extracorporeal and drug delivery system and method that reduces workload on doctors, nurses and caregivers.

It is another advantage of the present disclosure to provide a combined extracorporeal and drug delivery system and method that improves fluid removal accuracy.

It is a further advantage of the present disclosure to provide a combined extracorporeal and drug delivery system and method that improves drug dosage delivery accuracy.

It is still another advantage of the present disclosure to provide a combined extracorporeal and drug delivery system and method that may be implemented with existing equipment.

It is still a further advantage of the present disclosure to provide a combined extracorporeal and drug delivery system and method that modifies IV drug flowrate, and/or concentration.

It is yet another advantage of the present disclosure to provide a combined extracorporeal and drug delivery system and method that modifies IV drug flowrate or concentration based on effluent removal or dilution, e.g., due to replacement and/or dialysis fluid flowrates.

It is yet a further advantage of the present disclosure to provide a combined extracorporeal and drug delivery system and method that takes into account overlapping chemicals or constituents in the IV drug and replacement and/or dialysis fluids to see if the amount of the overlapping fluid in the IV drug is allowable, should be reduced or should be eliminated.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been selected principally for readability and instructional purposes, and not to limit the scope of the inventive subject matter.

DETAILED DESCRIPTION OF EXAMPLE EMBODIMENTS

Figure 1:
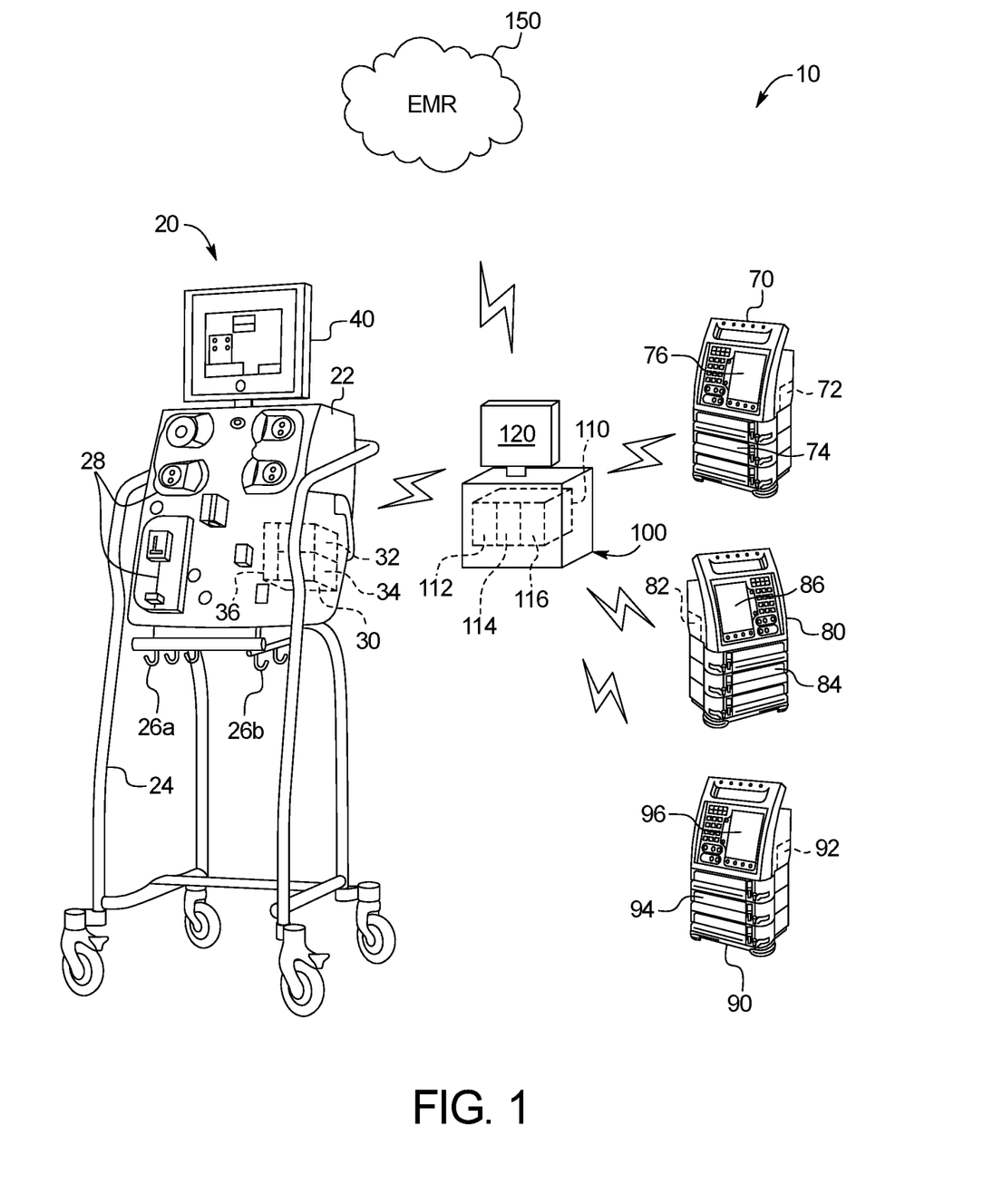
FIG. 1 is a perspective view of one embodiment of the combined extracorporeal and drug delivery system of the present disclosure.

Referring now to the drawings and in particular to FIG. 1, an embodiment of a combined extracorporeal and drug delivery system 10 of the present disclosure is illustrated. System 10 includes a renal failure therapy machine 20, such as a continuous renal replacement therapy ("CRRT") machine or an intermittent hemodialysis ("IHD") machine and intravenous ("IV") drug infusion pump 70, 80 and/or 90. Renal failure therapy machine 20 can for example perform type of renal therapy, such as arteriovenous hemofiltration, continuous arteriovenous hemodialysis, continuous arteriovenous hemodiafiltration, continuous venovenous hemofiltration, continuous venovenous hemodialysis, continuous venovenous hemodiafiltration, slow continuous ultrafiltration, hemoperfusion, therapeutic plasma exchange, cytopheresis, continuous ultrafiltration with periodic intermittent hemodialysis), treatment of fluid overloads, congestive heart failure, drug overdoses, poisonings, immune disorders, sepsis, acid imbalances and any combination thereof Renal failure therapy machine 20 in the illustrated embodiment includes a housing 22 supported by a rolling frame 24, so that renal failure therapy machine 20 may be moved or oriented to a position that is convenient for operation within a hospital room or intensive care unit ("ICU"). Renal failure therapy machine 20 in the illustrated embodiment includes scales 26a to . . . 26n, which enable the weight and thus the volume and flowrate of one or more fluid, such as dialysis fluid, replacement fluid, or effluent, to be determined. For instance, scale 26a may be used in one implementation to monitor the fresh dialysis fluid flow, while scale 26b is used to monitor the flow of effluent. Renal failure therapy machine 20 in the illustrated embodiment also includes exterior apparatuses 28 supported by housing 22, which may include for example pumps, pressure sensors, air detectors, blood leak detectors, valves such as tubing pinch valves, discussed in more detail.

Scales 26a to . . . 26n and all sensors of apparatuses 28 output to a control unit 30, which controls all electrically actuated devices 28 of renal failure therapy machine 20. Control unit 30 in the illustrated embodiment includes one or more processor 32 and one or more memory 34, video card, sound card, wireless transceiver or wired interface 36, and the like. Control unit 30 communicates with a coordinating logic implementor 100 wired or wirelessly. Any wired communication discussed herein may be via Ethernet or fiber optic connection, for example. Any wireless communication discussed herein may be performed via any of Bluetooth™, WiFi™, Zigbee®, Z-Wave®, wireless Universal Serial Bus ("USB"), radio frequency ("RF"), ultrasonic, photoelectric, microwave or infrared protocols, or via any other suitable wireless communication technology.

Renal failure therapy machine 20 in the illustrated embodiment also includes a graphical user interface ("GUI") 40, which enables an operator to enter data and commands into and/or receive information from control unit 30. GUI 40 includes a video monitor, which may likewise operate with a touch screen overlay placed onto the video monitor for inputting commands into control unit 30. GUI 40 may also include one or more electromechanical input device, such as a membrane switch or other button. Control unit 30 may also include an audio controller for playing sound files, such as alarm or alert sounds, at one or more speaker of renal failure therapy machine 20. Although GUI 40 is illustrated as being connected to housing 22, it is also possible that GUI 40 is separate from and communicates wirelessly with control unit 30 via any of the protocols described above.

Coordinating logic implementor 100 in the illustrated embodiment includes its own control unit 110. Control unit 110 in the illustrated embodiment includes one or more processor 112 and one or more memory 114, video card, sound card, and wireless transceiver or wired interface 116 for communicating with control unit 30 of renal failure therapy machine 20, and if enabled, the control units of IV drug infusion pump 70, 80 and/or 90.

Coordinating logic implementor 100 in the illustrated embodiment also includes a graphical user interface ("GUI") 120, which enables an operator to enter data and commands into and/or receive information from control unit 110. GUI 120 includes a video monitor, which may likewise operate with a touch screen overlay placed onto the video monitor for inputting commands into control unit 110. GUI 120 may also include one or more electromechanical input device, such as a membrane switch or other button. Control unit 110 may also include an audio controller for playing sound files, such as alarm or alert sounds, at one or more speaker of coordinating logic implementor 100.

Although coordinating logic implementor 100 is illustrated as being located adjacent to renal failure therapy machine 20, coordinating logic implementor 100 may alternatively be located on or connected to renal failure therapy machine 20. In a further alternative embodiment, coordinating logic implementor 100 is integrated within renal failure therapy machine 20, such that control unit 110 and its software and programming is integrated into control unit 30. Providing coordinating logic implementor 100 separate from renal failure therapy machine 20, however, allows coordinating logic implementor 100 to operate with existing renal failure therapy machines, perhaps with a software upgrade. It is contemplated to implement coordinating logic implementor 100 as a stand alone device, as part of any of the medical fluid machines, and/or as third party hardware, and/or as abstracted into software somewhere (like in an EMR, edge computing, cloud services, etc.).

IV drug infusion pumps 70, 80 and/or 90 each include a control unit 72, 82 and 92, respectively. Control units 72, 82 and 92 may each likewise include one or more processor, one or more memory, a video card, a sound card, and a wireless transceiver or wired interface for communicating with control unit 110 of coordinating logic implementor 100. IV drug infusion pumps 70, 80 and/or 90 each also include one or more pump actuator 74, 84 and 94 under control of control unit 72, 82, 92, respectively, such as a peristaltic, platen or other type of tubing or syringe pump actuator. IV drug infusion pumps 70, 80 and/or 90 each also include one or more graphical user interface ("GUI") 76, 86 and 96, respectively. Each GUI 76, 86 and 96 may include a video monitor, which may likewise operate with a touch screen overlay placed onto the video monitor for inputting commands into control unit 72, 82 and 92, respectively. Each GUI 76, 86 and 96 may also include one or more electromechanical input device, such as a membrane switch or other button.

Renal failure therapy machine 20 and external infusion pumps 70, 80 and 90 each, in one embodiment, include an address that distinguishes the machine and pumps from one another in the eyes of coordinating logic implementor 100. The addresses designate the pumps of renal failure therapy machine 20 and infusion pumps 70, 80 and 90 to be associated with a specific patient undergoing an AKI or other renal failure treatment. The addresses prevent miscommunication between multiple renal failure therapy machines 20 and associated infusion pumps 70, 80 and 90 if multiple treatments are taking place simultaneously and in close proximity to one another, e.g., for example, in adjacent ICU's or in a treatment center. The potential for miscommunication exists to a greater degree with wireless communication.

The addresses described above enable information to be transferred back and forth between coordinating logic implementor 100, renal failure therapy machine 20 and infusion pumps 70, 80 and 90. For example, current treatment data may be sent from either one or both of renal failure therapy machine 20 and infusion pumps 70, 80 and 90 to coordinating logic implementor 100. Coordinating logic implementor 100 may send one or more determined operating parameter to renal failure therapy machine 20 and to one or more of infusion pumps 70, 80 or 90 for (i) automatic entry and actuation by a respective control unit 30, 72, 82 or 92 and/or (ii) display at a respective GUI 40, 76, 86 or 96 for approval or acceptance. In a further alternative embodiment, coordinating logic implementor 100 may display one or more determined operating at its GUI 120 alternatively or in addition to the display at GUI 40, 76, 86 or 96.

The following scenarios are contemplated for system 10 and associated methodology: (i) there is communication between coordinating logic implementor 100 and renal failure therapy machine 20, and system 10 has been authorized to allow automatic inputting and actuation of one or more operating parameter sent from coordinating logic implementor 100 to renal failure therapy machine 20; (ii) there is communication between coordinating logic implementor 100 and infusion pump 70, 80 or 90, and system 10 has been authorized to allow automatic inputting and actuation of one or more operating parameter sent from coordinating logic implementor 100 to infusion pump 70, 80 or 90; (iii) there is communication between coordinating logic implementor 100 and renal failure therapy machine 20, but system 10 has not been authorized to allow automatic inputting and actuation of one or more operating parameter sent from coordinating logic implementor 100 to renal failure therapy machine 20, so that the one or more parameter is displayed at one or more of GUI 40 or 120 as a suggested parameter to the operator; (iv) there is communication between coordinating logic implementor 100 and infusion pump 70, 80 or 90, but system 10 has not been authorized to allow automatic inputting and actuation of one or more operating parameter sent from coordinating logic implementor 100 to infusion pump 70, 80 or 90, so that the one or more parameter is displayed at one or more GUI 120, 76, 86 or 96 as a suggested parameter to the operator; and (v) there is no communication between coordinating logic implementor 100 and infusion pump 70, 80 or 90, so that one or more parameter determined by coordinating logic implementor 100 is displayed at one or more GUI 120 or 40 (of machine 20) as a suggested IV drug parameter to the operator. In the latter scenario (v), the prescribed dose or flowrate corresponding to a prescribed drug dose is initially entered manually into coordinating logic implementor 100 via GUI 120 or renal failure therapy machine 20 via GUI 40.

FIG. 1 further illustrates that system 10 contemplates that coordinating logic implementor 100 be configured to communicate with the hospital's electronic medical record ("EMR") database 150, e.g., wired or wirlessly. In an embodiment, at the end of a CRRT or IHD treatment and associated drug delivery, any or all relevant treatment data is sent from coordinating logic implementor 100 to EMR database 150, which stores a file for the patient. Other treatment information, such as the drugs delivered, alarms, alerts, caregiver or operator notes entered during treatment, may also be sent, e.g., date- and time-stampped, from coordinating logic implementor 100 to EMR database 150.

Figure 2:
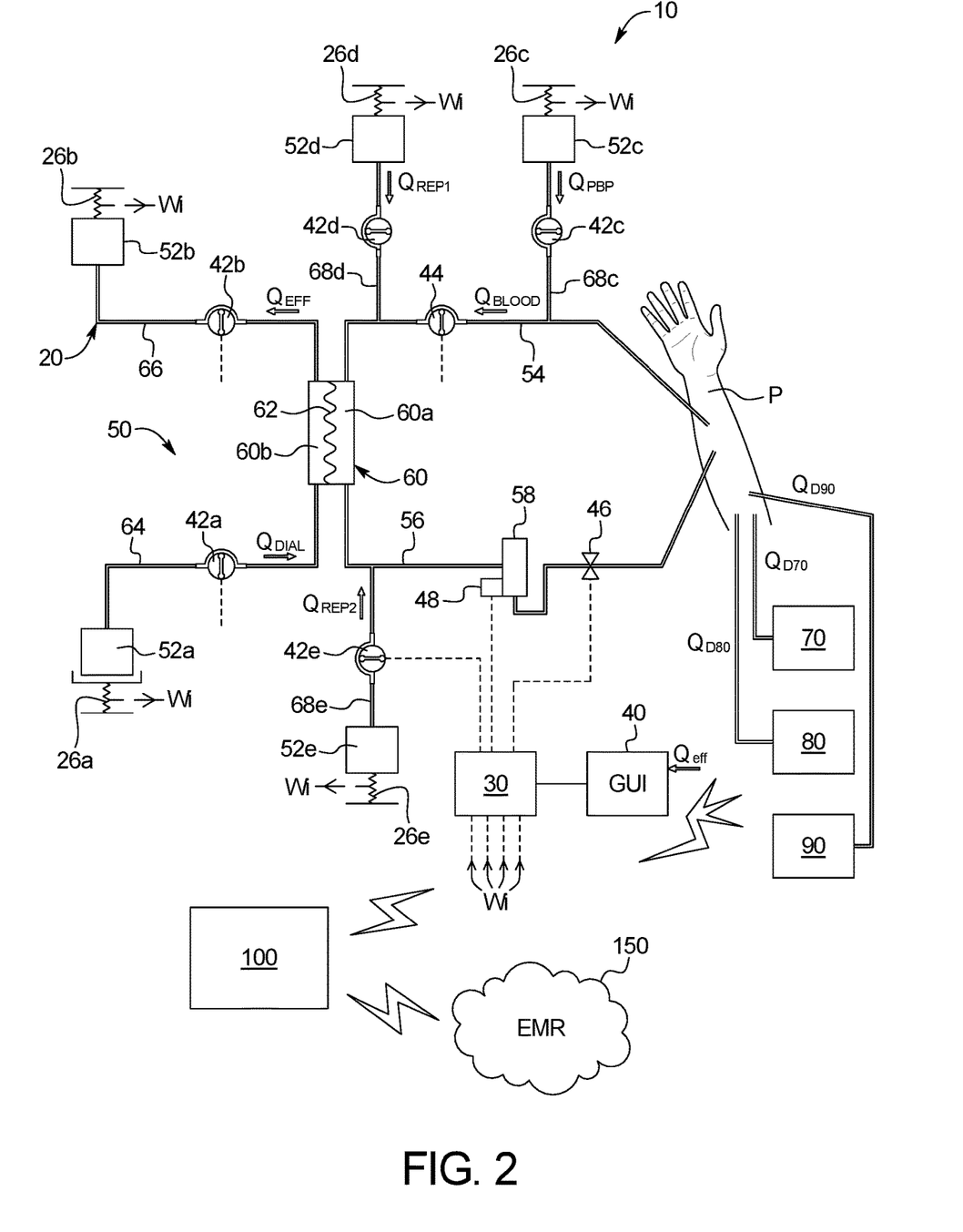
FIG. 2 is a schematic view of one embodiment of the combined extracorporeal and drug delivery system of the present disclosure.

Referring now to FIG. 2, system 10 is illustrated schematically to show one embodiment of the different types of fluid inputs that may affect the overall effluent flowrate determination. System 10 in FIG. 2 includes renal failure therapy machine 20, coordinating logic implementor 100 and infusion pumps 70, 80 and 90 as described in connection with FIG. 1. FIG. 2 also illustrates fresh dialysis fluid scale 26a and effluent scale 26b described in connection with FIG. 1 along with additional scales, namely, upstream predilution scale 26c, downstream predilution scale 26d and postdilution scale 26e. Coordinating logic implementor 100 is in communication with EMR database 150 as illustrated in FIG. 2.

Scales 26a to 26e respectively weigh fluid residing within dialysis fluid container 52a, effluent container 52b, upstream predilution container 52c, downstream predilution container 52d and postdilution container 52e. Containers 52a to 52c form a portion of a disposable set 50, which attaches to housing 22 (of FIG. 1) of renal failure therapy machine 20 for treatment. Disposable set 50 in the illustrated embodiment also includes an arterial line 54 for removing blood from a patient P, a venous line 56 for returning blood to patient P, and a drip chamber 58 placed in venous line 56 for removing any air from the blood before returning to patient P. A blood filter or dialyzer 60 seperates arterial line 54 from venous line 56. Blood filter or dialyzer 60 includes a blood compartment 60a, a dialysis fluid compartment 60b, which are separated by a semipermeable membrane 62. Arterial line 54 leads to blood compartment 60a, while venous line 56 extends from blood compartment 60a. Similarly, a fresh dialysis fluid line 64 extends from dialysis fluid container 52a to dialysis fluid compartment 60b, while effluent line 66 extends from dialysis fluid compartment 60b to effluent container 52b.

Disposable set 50 in the embodiment of FIG. 2 also includes an upstream predilution line 68c extending from upstream predilution container 52c to arterial line 54, a downstream predilution line 68d extending from downstream predilution container 52d to arterial line 54, and a postdilution line 68e extending from postdilution container 52e to venous line 56.

FIG. 1 generalizes pumps, sensors and valves, etc., associated with housing 22 of renal failure therapy machine 20 as exterior apparatuses 28. Those exterior apparatuses are illustrated in more detail in FIG. 2 as including a fresh dialysis fluid pump 42b operating with fresh dialysis fluid line 64, an effluent pump 42b operating with effluent line 66, an upstream predilution pump 42c operating with upstream predilution line 68c, a downstream predilution pump 42d operating with downstream predilution line 68d, and a postdilution pump 42e operating with postdilution line 68e. Additonally, a blood pump 44 is provided, which pumps blood from patient P along arterial line 54, through blood filter 60 and back to patient P via venous line 56. Plural valves are provided, such as venous valve 46. A level detector 48 is also provided to detect a liquid level in drip chamber 58.

All pumps, valves, detectors, scales, sensors and the like are under control of, or send output signals to, control unit 30 as illustrated by the dashed lines in FIG. 2. FIG. 2 illustrates a CRRT embodiment for renal failure therapy machine 20. An IHD or hemodialysis embodiment for renal failure therapy machine 20 would look much the same, but may instead (i) have online dialysis fluid generation and a house drain as opposed to containers 26a and 26b, (ii) use different types of pumping and valving (e.g., peristaltic and pinch used for CRRT as illustrated, or pneumatic and/or electromechanical for IHD), (iii) use volumetric or flowrate determination versus CRRT's weight detection for fluid control and balancing, and (iv) not deliver treatment fluid to blood lines 54 or 56. CRRT accordingly presents a most-case scenario for the number of different types of fluids that may be inputted into the effluent equation shown below, thereby providing support for IHD embodiments as well. It should be appreciated however that CRRT of system 10 does not have to use replacement fluid or can have one or both predilution and/or postdilution replacement fluids. Additionally, CRRT may or may not have dialysis fluid flow. CRRT of system 10 may have any combination of such fluid flows.

The flowrates associated with the different pumping sources in FIG. 2 are illustrated and include $Q_{BLOOD}$ for blood flow, $Q_{DIAL}$ for fresh dialysis fluid flow, $Q_{EFF}$ for effluent flow, $Q_{PBP}$ for pre-blood pump flow (e.g., heparin anticoagulant), $Q_{REP1}$ for predilution replacement fluid flow, $Q_{REP2}$ for postdilution replacement fluid flow, $Q_{D70}$ for infusion pump 70's drug flow, $Q_{D80}$ for infusion pump 80's drug flow and $Q_{D90}$ for infusion pump 90's drug flow. Except for $Q_{BLOOD}$ for blood flow, system 10 takes into account each of $Q_{DIAL}$, $Q_{PBP}$, $Q_{REP1}$, $Q_{REP2}$, $Q_{70}$, $Q_{80}$, and $Q_{90}$ in determining effluent flow $Q_{EFF}$. $Q_{DIAL}$, $Q_{PBP}$, $Q_{REP1}$, and $Q_{REP2}$ in an embodiment are prescribed by a doctor along with a prescribed patient fluid loss or ultrafiltration removal flow rate $Q_{UF}$. The drug for $Q_{70}$, $Q_{80}$, and $Q_{90}$ may be a flowrate that corresponds to a dose prescribed by a doctor or may be adjusted from the prescribed flowrate as discussed in detail below.

An overall fluid balance equation for system 10 in FIG. 2 is as follows:

$$Q_{UF}=Q_{EFF}-[Q_{DIAL}+Q_{PBP}+Q_{REP1}+Q_{REP2}+Q_{D70}+Q_{D80}+Q_{D90}]$$

In one example, $Q_{UF}$=200 ml/hr, $Q_{DIAL}$=1000 ml/hr, $Q_{PBP}$=600 ml/hr, $Q_{REP1}$=800 ml/hr, and $Q_{REP2}$=800 ml/hr. The drug flowrates are determined initially from the dosage prescribed by the doctor. The dosages may be provided in a form such as mg/(kg of patient weight) over a number of hours, which knowing the patient's weight gives g/hr, and knowing the density of the drug yields ml/hr. Assuming for the present example that $Q_{D70}$ is 60 ml/hr, $Q_{D80}$ is 100 ml/hr and $Q_{90}$ is 80 ml/hr, the above equation is populated as follows:

$$200=Q_{EFF}-[1000+600+800+800+60+100+80]$$
$$200=Q_{EFF}-[3440 \text{ (total patient fluid input)}]$$
$$Q_{EFF}=3640 \text{ ml/hr}$$

Notably, the 240 ml/hr total drug component (60+100+80) in the above calculation represents seven percent of the total patient fluid input of 3440 ml/hr, which is relatively significant, yielding a like percentage increase in effluent accuracy. In an embodiment, the above calculation is performed at coordinating logic implementor 100, which is able to obtain all input information from all doctor prescribed information either (i) electroncially from renal failure therapy machine 20 and/or infusion pumps 70, 80 and 90, (ii) entered manually at GUI 120, or (iii) some combination thereof.

Knowing the effluent, $Q_{EFF}$=3640 ml/hr, based on the prescribed dosages for the three drugs of infusion pumps 70, 80 and 90, system 10 now compensates for drug fractions that are removed via effluent flow $Q_{EFF}$. Coordinating logic implementor 100 receives the weight of patient P at the beginning of treatment and uses a conversion algorithm to compute the patient's corresponding blood volume. Assuming patient P to weigh 80 kg, one estimator (https://reference.medscape.com/calculator/estimated-blood-volume) estimates the blood volume of patient P to be 6000 ml. Knowing that 3440 ml will be added over the next hour, the cumulative volume totals 9440 ml. The percentage of each drug in the volume over the hour is then (i) 60/9440 or 0.63% for the drug of infusion pump 70, (ii) 100/9440 or 1.1% for the drug of infusion pump 80, and 80/9440 or 0.84% for the drug of infusion pump 90.

Coordinating logic implementor 100 then increases the actual flowrates for each infusion pump 70, 80 and 90, so that over the hour the drug received by the patient achieves the prescribed dosage. In the example, the flowrate for pump 70 would increase from 60 ml/hr to 60.38 ml/hr (0.63% increase). The flowrate for pump 80 would increase from 100 ml/hr to 101 ml/hr (1.1% increase). The flowrate for pump 90 would increase from 80 ml/hr to 80.67 ml/hr (0.84% increase). Assuming the flowrate adjustment to be relatively small, as here, the calculation for effleunt flowrate $Q_{EFF}$ does not need to be performed again. It is contemplated for larger drug flowrate adjustments, however, that system 10 takes adjustments into account in determining $Q_{EFF}$ in the manner above. The drug flowrate adjustments from a drug standpoint are important however because the patient is now receiving the prescribed amount of the drugs.

In determining whether to adjust the flowrate for an IV drug, coordinating logic implementor 100 may take into account whether CRRT or IHD machine 20 is actually running. For example, if the IV drug is delivered before or after CRRT or IHD treatment, coordinating logic implementor 100 does not adjust, or suggest to adjust, the IV drug flowrate from the flowrate associated with the prescribed dosage. If CRRT or IHD machine 20 is stopped for whatever reason during treatment, e.g., due to an alarm, alert, supply bag change, etc., machine 20 communicates same (e.g., wired or wirelessly) to coordinating logic implementor 100, which may be programmed to react in any of a plurality of alternative ways, for example, (i) cause at least one infusion pump 70, 80, 90 to automatically reduce, or suggest for reduction at the at least one infusion pump 70, 80, 90, its IV drug flowrate as described herein while the stoppage persists, (ii) maintain the at least one IV drug flowrate at the elevated flowrate during the stoppage but count the additional flowrate as being part of the administered dosage, and communicate same to at least one infusion pump 70, 80, 90 or to an oprator of same, so that overall drug delivery time may be reduced to meet the prescribed dosage, or (iii) shut down one or more infusion pump 70, 80, 90 completely, e.g., if its drug is meant to accompany the CRRT or IHD treatment, e.g., if the drug is an anticoagulant, phosphorous supplement, and the like.

In an embodiment, all enabled communication is two-way, so that coordinating logic implementor 100 will know when, during operation of renal failure therapy machine 20, one or more infusion pump 70, 80, 90 is operating. In an embodiment, logic implementor 100 periodically polls (e.g., every second, multiple seconds, or fraction of a second) control unit 72, 82, 92 of infusion pump 70, 80, 90, respectively, whether it is currently in a pumping mode or not. Control unit 72, 82, 92 responds appropriately back to control unit 110 of coordinating logic implementor 100, which reacts accordingly. In the example above for determining $Q_{EFF}$, logic implementor 100 during operation of renal failure therapy machine 20 and knowing $Q_{D70}$ is 60 ml/hr, $Q_{D80}$ is 100 ml/hr and $Q_{90}$ is 80 ml/hr, will (i) automatically increase/reduce, or suggest to increase/reduce, $Q_{EFF}$ by 60 ml/hr when infusion pump 70 commences/stops pumping, (ii) automatically increase/reduce, or suggest to increase/reduce, $Q_{EFF}$ by 100 ml/hr when infusion pump 80 commences/stops pumping, and (iii) automatically increase/reduce, or suggest to increase/reduce, $Q_{EFF}$ by 80 ml/hr when infusion pump 90 commences/stops pumping.

To the extent that any one of infusion pump 70, 80, 90 commensing or stopping pumping appreciably affects total patient fluid input (3440 ml/hr in the example above), coordinating logic implementor 100 is configured to adjust up or down, or to suggest same, the flowrate of any other infusion pump 70, 80, 90 currently running. In this manner, system 10 is configured to adjust the operation of any infusion pump 70, 80, 90 based on the current state (e.g., pumping versus not pumping) of any other infusion pump 70, 80, 90.

The above examples involve the adjustment of IV drug flowrate to compensate for a portion of a prescribed drug being removed from the patient as effluent fluid of a renal failure therapy instead of being absorbed by and therfore treating the patient. Another way to compensate for the effluent removal according to the present disclosure is to adjust the concentration of the IV drug so that the amount of drug actually absorbed by the patient matches that which is prescribed. In the example above, (i) the amount or percentage of the IV drug of infusion pump 70 lost over an hour is 0.63%, (ii) the amount of the IV drug of infusion pump 80 lost over the hour is 1.1%, while (iii) the amount of the IV drug of infusion pump 90 lost over the hour is 0.84%. It is accordingly contemplated that coordinating logic implementor 100 make a suggestion to the physician, technician, machine operator, etc., to increase the concentration of the IV drug by the percentage lost, so that the patient receives the prescribed amount of each IV drug despite losing some of the drug to effluent removal of the renal failure therapy. In an example, if the concentration of (i) the IV drug of infusion pump 70 is 20% by volume, then its concentration is increased by 0.63% to 20.13% by volume, (ii) the IV drug of infusion pump 80 is 10% by volume, then its concentration is increased by 1.1% to 10.11% by volume, and (iii) the IV drug of infusion pump 90 is 12% by volume, then its concentration is increased by 0.84% to 12.1% by volume.

The above example assumes that the prescribed flowrate is not adjusted, namely, that $Q_{D70}$ remains at 60 ml/hr, $Q_{D80}$ remains at 100 hr and $Q_{90}$ remains at 80 hr using the adjusted concentrations. It is contemplated for coordinating logic implementor 100 of system 10 in another alternative embodiment to provide a combination of an adjusted flowrate and an adjusted concentration so that the prescribed dose is met even though some of the IV drug is removed via the effluent flow.

Many hospitals have sophisticated compounding systems or units that are able to achieve highly accurate concentrations, such as those specified above. Adjusting concentration versus flowrate may be advantageous when, for example, the prescribed flowrate is at a maximum allowable flowrate for the drug and/or for the infusion pump 70, 80, 90. The adjustment of concentration may require coordinating logic implementor 100 to suggest to the physician or caregiver, etc., that the concentration change be made, as opposed to automatic concentration adjustment, so that the physician or caregiver, etc., may order the IV drug having the adjusted concentration from the hospital's pharmacy. As with any suggestion from coordinating logic implementor 100 discussed herein, the suggestion may be provided audibly, visually or audiovisually at any one or more of GUI 40 of renal failure therapy machine 20, GUI 120 of coordinating logic implementor 100, and/or GUI's 76, 86 and 96 of associated infusion pumps 70, 80, 90.

Figure 3:
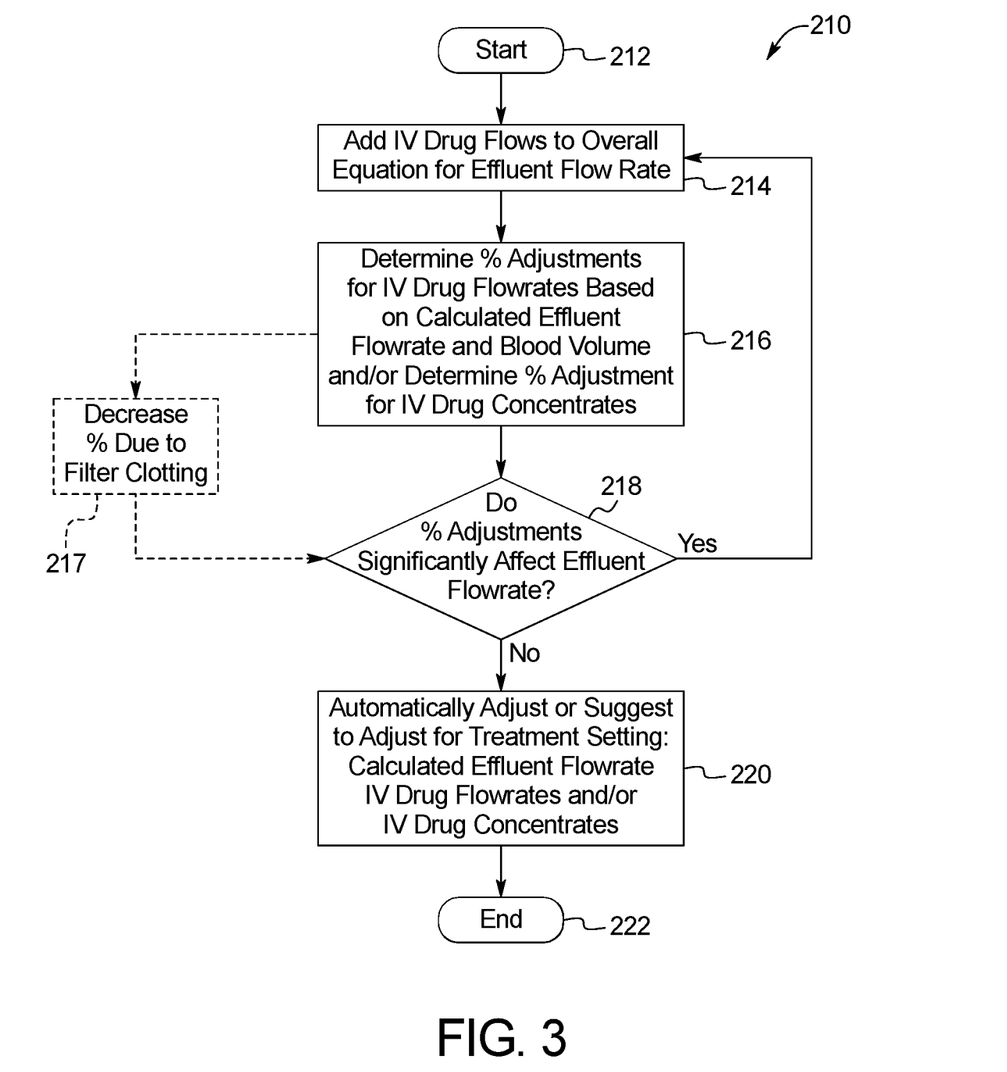
FIG. 3 is a schematic flowchart illustrating example does correction adjustments that may be made according to the combined extracorporeal and drug delivery system of the present disclosure.

Method 210 of FIG. 3 summarizes the above-described adjustments (automatic or suggested) determined by coordinating logic implementor 100 of system 10. In an embodiment, method is implemented at control unit 110 of coordinating logic implementor 100. At oval 212, method 210 begins. At block 214, control unit 110 adds the IV drug pump flowrates (e.g., $Q_{70}$, $Q_{D80}$ and $Q_{D90}$) to the overall equation for effluent flowrate ($Q_{EFF}$) and effluent flowrate ($Q_{EFF}$) is calculated as illustrated above.

At block 216, control unit 110 determines (i) a perecentage adjustment for each IV drug flowrate ($Q_{70}$, $Q_{80}$, $Q_{D90}$) using the calculated effluent flowrate and the patient's blood volume in a manner described above and/or (ii) determines a concentration adjustment for the IV drugs of infusion pumps 70, 80, 90 in a manner described above. The adjustments may be implemented automatically or be suggested to the caregiver as discussed herein.

At diamond 218, control unit 110 determines whether the perecentage adjustments, if made, for the IV drug flowrates ($Q_{70}$, $Q_{80}$, $Q_{D90}$) when taken collectively significantly affect the calculation for effluent flowrate ($Q_{EFF}$) performed at block 214. "Significantly" may be determined by comparing the collective adjustment of IV drug flowrates ($Q_{70}$, $Q_{80}$, $Q_{D90}$) as a percentage of a currently calculated effluent flowrate ($Q_{EFF}$) to a threshold percentage (e.g., 0.5%). If the percentage adjustment meets or exceeds the threshold percentage, then the affect is considered "significant" according to diamond 218. In the example above, $Q_{EFF}$ is determined to be 3640 ml/hr, while the flowrate for (i) pump 70 is adjusted from 60 ml/hr to 60.38 ml/hr, (ii) pump 80 is adjusted from from 100 ml/hr to 101 ml/hr, and pump 90 is adjusted from 80 ml/hr to 80.67 ml/hr. The total or collective adjustment of the IV pumps is 2.05 ml/hr (0.38 ml/hr+1.00 ml/hr+0.67 ml/hr), which as a percentage of the currently calculated $Q_{EFF}$ of 3640 ml/hr is 0.06%, and which is well below an example threshold percentage (e.g., 0.5%).

If the perecentage adjustments for the IV drug flowrates significantly affect the calculation for effluent flowrate ($Q_{EFF}$) as determined at diamond 218, then method 210 returns to block 214 and updates effluent flowrate ($Q_{EFF}$) and to block 216 to update the flowrate adjustments for the IV pumps. The loop between diamond 218 and blocks 214 and 216 continues until the perecentage adjustments for the IV drug flowrates do not significantly affect the calculation for effluent flowrate ($Q_{EFF}$) as determined at diamond 218, at which point method 210 proceeds to block 220. At block 220, control unit 110 causes the adjustments determined at block 216 to be implemented automatically or suggests the adjustments to the caregiver in any of the manners described herein. At diamond 222, method 210 ends.

Dashed block 217 illustrates and option for method 210 in which blood filter 60 (e.g., dialyzer or hemofilter) patency or lifespan is taken into consideration. In both CRRT and IHD, the dialyzer or hemofilter 60 is known to clot slowly over time, which may decrease the rate of drug removal despite the flow rates being set as constants at renal failure therapy machine 20. The amount of clotting may be estimated by sensing pressure in one or more of effluent line 66, arterial line 54 and/or venous line 56. For example, if the pressure in effluent line 66 builds over the course of treatment, it may be assumed to be from the clotting of blood filter 60. The pressure build may be correlated, e.g., empirically, with a percentage decrease in drug removal. The correlation is in one embodiment stored as a lookup table in control unit 110 of coordinating logic implementor 100. Here, as coordinating logic implementor 100 receives increasing pressure signals from a pressure sensor operating with effluent line 66 over the course of a treatment, coordinating logic implementor 100 finds the corresponding percentage decrease of drug removal from the lookup table and reduces the percentage adjustment for IV drug flowrate and/or IV drug concentration determined in block 216 accordingly.

Method 210 adjusts IV drug flowrates based on the fact that a patient undergoing a renal failure therapy treatment may be undergoing fluid removal in the form of ultrafiltration as effluent fluid. Such fluid removal is presumed to also remove a portion of one or more IV drug, which is otherwise intended to treat the patient. Method 210 highlights two ways to adjust for the IV drug removal due to effluent removal. It should be appreciated however that the present disclosure contemplates other ways to compensate for IV drug removal or dilution that do not involve effluent flowrate ($Q_{EFF}$).

In one alternative way, IV drug flowrates $Q_{70}$, $Q_{80}$, and $Q_{90}$ (and/or concentrations) are adjusted (or suggested to be adjusted by coordinating logic implementer 100) instead based on an amount that the drugs are diluted by the $Q_{REP1}$ for predilution replacement fluid flow and $Q_{REP2}$ for postdilution replacement fluid flow. Here, the IV drug flowrates $Q_{70}$, $Q_{80}$, and $Q_{90}$ may increase, for example, by a percentage equal to the drug flowrate divided by the total replacement fluid flowrate plus the drug flowrate. For example, using the same example flowrate data from above, where $Q_{REP1}$ is 800 ml/hr, $Q_{REP2}$ is 800 ml/hr, $Q_{D7}$ is 60 ml/hr, $Q_{D80}$ is 100 ml/hr and $Q_{90}$ is 80 ml/hr, then (i) $Q_{D70}$ is increased by 60 ml/hr/(800 ml/hr+800 ml/hr+60 ml/hr) or 3.6%, (ii) $Q_{D80}$ is increased by 100 ml/hr/(800 ml/hr+800 ml/hr+100 ml/hr) or 5.9%, while (iii) $Q_{90}$ is increased by 80 ml/hr/(800 ml/hr+800 ml/hr+80 ml/hr) or 4.8%. So to make up for the fact that the three IV drugs are diluted during treatment by the predilution and postdilution replacement fluid flows, the flowrate of $Q_{D70}$ is increased from 60 ml/hr to 62.2 ml/hr (by 3.6%). The flowrate of $Q_{D80}$ is increased from 100 ml/hr to 106 ml/hr (by 5.9%). The flowrate of $Q_{90}$ is increased from 80 ml/hr to 83.8 ml/hr (by 4.8%). It should be appreciated that those of skill may determine other ways to compensate for IV drug dilution due to replacement fluid flow other than the example compensation just described, and that IV drug concentration may be adjusted alternatively or additionally due to IV drug dilution as just described.

As is known, predilution replacement fluid and postdilution replacement fluid are used in hemofiltration ("HF") and hemodialfiltration ("HDF") treatments, either for CRRT or IHD. In HF, there is no dialysis fluid flow, $Q_{DIAL}$. HD and HDF do employ dialysis fluid flow, $Q_{DIAL}$. In theory, dialysis fluid flow does not add to the patient's overall blood volume due to the fact that dialysis fluid flow is passed along the outsides of the dialyzer membranes whose tiny hollow fiber pores block the dialysis fluid from entering the blood sides of the membranes. In such a case, dialysis fluid flowrate $Q_{DIAL}$ does not dilute the IV drug flowrates. With high flux dialyzers, however, it is likely, if not expected, that some percentage of the dialysis fluid will migrate into the extracorporeal circuit and thus into the patient's blood volume. If the amount of the migration becomes significant enough, for example, in the case of chronic HD in which dialysis fluid flowrates are specified in ml/min as opposed to the example $Q_{DIAL}$ of 1000 ml/hr discussed above, then IV drug flow dilution due to dialysis fluid flow may present itself. In such a situation, IV drug flow dilution due to dialysis fluid flow may be compensated for in the same manners (flowrate and/or concentration) described above for predilution replacement fluid and postdilution replacement fluid.

In compensating for IV drug flow dilution due to dialysis fluid flow, coordinating logic implementer 100 estimates the amount or flowrate of dialysis fluid migrating from the dialysis fluid compartment of the dialyzer into the blood compartment of the dialyzer. The estimation ($Q_{EST}$) may take into account, and therefore vary due to, any one or more of: the amount of flux or openness of the dialyzer membranes, the blood flowrate, the dialysis fluid flowrate, a relationship between the blood flowrate and the dialysis fluid flowrate, the pressure of blood flow through the dialyzer, the pressure of dialysis fluid flow through the dialyzer, and/or a relationship between the pressure of blood flow and dialysis fluid flow through the dialyzer (e.g., transmembrane pressure). Once coordinating logic implementer 100 establishes $Q_{EST}$, then the IV drug flowrates $Q_{70}$, $Q_{80}$, and $Q_{90}$ may be increased (or suggested to be increased via the coordinating logic implementer), for example, by a percentage equal to the drug flowrate divided by $Q_{EST}$ plus the drug flowrate. As with any suggestion from coordinating logic implementer 100 discussed herein, the IV drug flowrate suggestions here may be provided audibly, visually or audiovisually at any one or more of GUI 40 of renal failure therapy machine 20, GUI 120 of coordinating logic implementer 100, and/or GUI's 76, 86 and 96 of associated infusion pumps 70, 80, 90.

In a further alternative aspect of the present disclosure, the chemical formulation of an IV drug is modified due to, for example, chemical overlap with the formulation of the predilution replacement fluid, postdilution replacement fluid, and/or dialysis fluid. As discussed above, many hospitals have sophisticated compounding systems or units that are able to achieve highly accurate concentrations. It is therefore possible to adjust the chemical makeup of an IV drug to avoid duplication of a particular chemical substance with that of renal therapy replacement fluid or dialysis fluid. For example, renal therapy replacement fluids and IV drug fluids may both contain phosphate. System 10 here is configured to look at both phosphate doses to see if they can coexist or if a modification to the IV drug phosphate constituency needs to be made.

If providing both renal therapy replacement and IV drug fluids treatment fluids to the patient during a same hospital treatment (either directly simultaneously or close together enough that phosphate or other overlapped constituent from the two sources is present in the patient simultaneously), then it is desirable and contemplated that coordinating logic implementer 100 of system 10 be configured to (i) know the chemical compositions of both the renal therapy replacement fluid(s) and the IV drug, (ii) identify and combine the doses or flowrates of the overlapping constituents or chemicals of the renal therapy replacement fluid(s) and the IV drug, (iii) determine if the combined dose or flowrate exceeds a maximum dose or flowrate for each overlapping constituent or chemical, or determine if the dose or flowrate of the constituent or chemical should not exceed that of the IV drug prescription at all, and (iv) if the amount of the constituent or chemical in the renal therapy replacement fluid should be reduced or eliminated, notify the clinician, doctor or other user of system 10 and/or the hospital pharmacy, so that the IV drug is so modified. As with any suggestion from coordinating logic implementer 100 discussed herein, the IV drug constituent suggestions here may be provided audibly, visually or audiovisually at any one or more of GUI 40 of renal failure therapy machine 20, GUI 120 of coordinating logic implementer 100, and/or GUI's 76, 86 and 96 of associated infusion pumps 70, 80, 90.

In an example, suppose that the prescribed dose of phosphate for patient P is X mg/(kg (patient weight) * hr), that the dose of phosphate received from the renal replacement fluid ($Q_{REP1}$ plus $Q_{REP2}$) is X/3, and that the dose of phosphate that patient P actually receives should not exceed the prescribed dose. Here, control unit 110 of coordinating logic implementor 100 is programmed to (i) accept and know the prescribed dose of phosphate for patient P (X mg/kg (patient weight) * hr, (ii) accept and know that the actual dose of phosphate is not to exceed the prescribed dose, (iii) accept and know the patient's weight (e.g., taken prior to treatment and delivered directly, wired or wirelessly to coordinating logic implementor 100) and thus be able to determine X, (iv) accept and know the chemical constituency of replacement fluid 1 and/or replacement fluid 2 (whichever one or both are used), (v) accept and know the prescribed flowrate of replacement fluid 1 and/or replacement fluid 2, (vi) calculate the dose of replacement fluid 1 and/or replacement fluid 2 knowing the replacement fluid chemical constituency and the weight of patient P, (vii) offset (or eliminate) the amount of phosphate in the IV drug knowing the replacement fluid dose to achieve the prescribed dose, and (viii) communicate the updated chemical formula for the IV drug having the offset amount of constituency of phosphate in any manner discussed herein. In the example above, the constituency of the IV drug is changed from having X mg/(kg (patient weight) * hr) dose of phosphate to 2×/3 mg/(kg (patient weight) * hr) dose of phosphate, so that when delivered in combination with replacement fluid 1 and/or replacement fluid 2 having X/3 mg/(kg (patient weight) * hr) dose of phosphate, the resulting dose of phosphate delivered is the prescribed dose X mg/(kg (patient weight) * hr).

Control unit 110 of coordinating logic implementor 100 may alternatively be programmed to allow patient P to receive the additional X/3 mg/(kg (patient weight) * hr) dose of phosphate from replacement fluid 1 and/or replacement fluid 2. Or, control unit 110 of coordinating logic implementor 100 may determine that the dose of phosphate from replacement fluid 1 and/or replacement fluid 2 exceeds that of the prescribed dose of the IV drug in which case, control unit 110 of coordinating logic implementor 100 generates an alarm or alert in any of the manners and to any of the destinations discussed herein. The above teachings using replacement fluid apply equally to dialysis fluid assuming a certain and quantifiable amount of dialysis fluid migrates into the extracorporeal circuit as discussed above. It should be appreciated that the constituency of replacement fluid 1 and/or replacement fluid 2 may be modified instead or additionally to the modification of the constituency of the IV drug, for example, if the replacement fluid is made online at or near renal failure therapy machines 20. It is often the case however that the replacement fluids are premade, bagged and sterilized. The previous paragraphs apply to any overlapping chemical or constituent and are in no way limited to phosphate.

Figure 4:
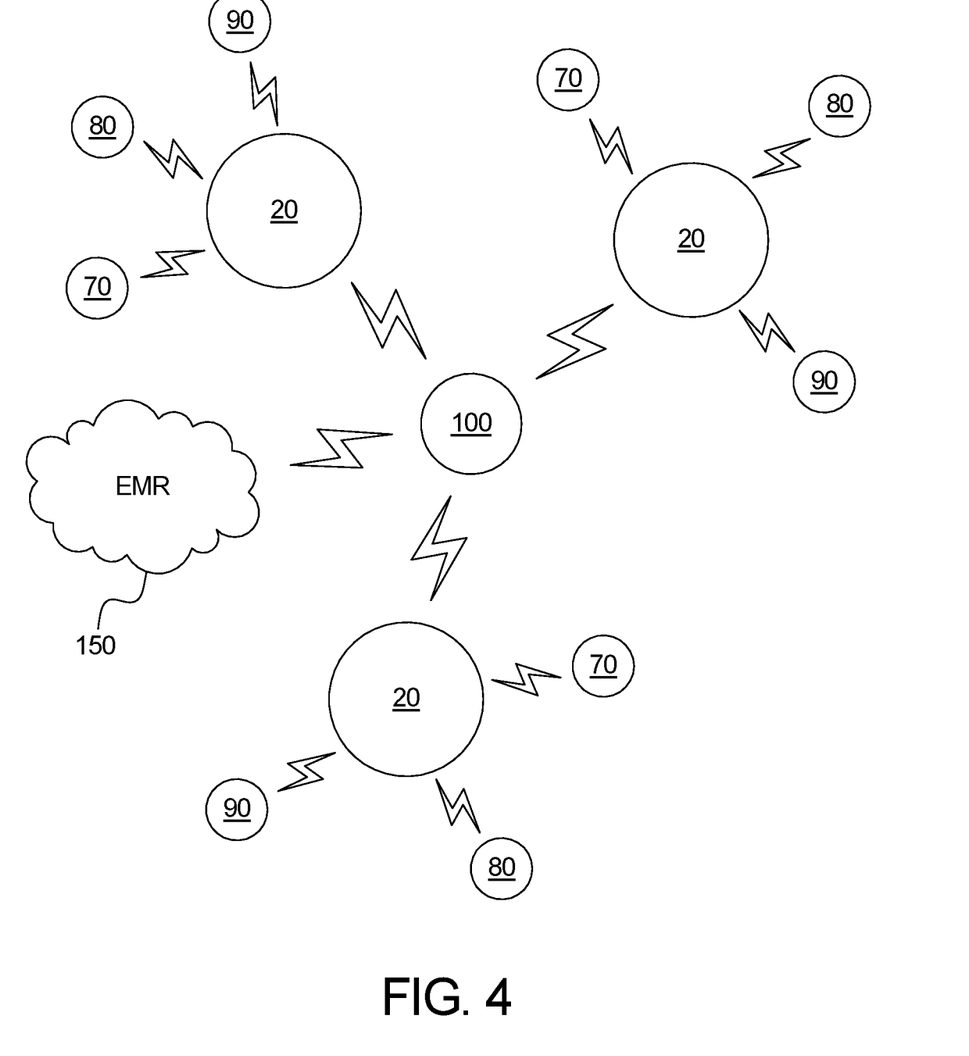
FIG. 4 is a schematic view of one embodiment of the combined extracorporeal and drug delivery system of the present disclosure.

Referring now to FIG. 4, an embodiment of system 10 shows a single coordinating logic implementor 100 operating in the manner described above with multiple clusters of renal failure therapy machines 20 and their associated infusion pumps 70, 80, 90. In one embodiment, logic implementor 100 is the hub for all spoke renal failure therapy machines 20 and all spoke infusion pumps 70, 80, 90, which is the case with FIGS. 1 and 2. FIG. 4 illustrates an alternative embodiment. Here, coordinating logic implementor 100 is illustrated as being a higher level hub to each of the spoke CRRT or IHD machines 20 in its cluster, wherein CRRT or IHD machines 20 are in turn lower lever hubs to their associated spoke infusion pumps 70, 80, 90. Coordinating logic implementor 100 is in communication with EMR database 150 as illustrated in FIG. 4. The arrangment of FIG. 4 may be preferred when shorter range wireless communication is provided. Here, for example, (i) treatment parameters or states are communicted from infusion pumps 70, 80, 90 to coordinating logic implementor 100 via the corresponding renal failure therapy machine 20, and (ii) operating parameters (automatic or suggested) are determined at and communicted from coordinating logic implementor 100 to infusion pumps 70, 80, 90 via the renal failure therapy machine 20.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. An extracorporeal and drug delivery system comprising:
    a renal failure therapy machine operable with a blood filter in fluid communication with an arterial line for removing blood from a patient to the blood filter and a venous line for returning blood from the blood filter to the patient, the renal failure therapy machine including
        an effluent pump positioned and arranged to pump effluent from the blood filter at an effluent flowrate, and
        at least one of
            a dialysis fluid pump positioned and arranged to pump dialysis fluid to the blood filter at a dialysis fluid flowrate,
            a predilution pump positioned and arranged to pump replacement fluid into the arterial line at a predilution flowrate, or
            a postdilution pump positioned and arranged to pump replacement fluid into the venous line at a postdilution flowrate;
    an infusion pump operable to deliver an intravenous ("IV") drug to the patient at an IV drug flowrate; and
    a coordinating logic implementor configured to:
        determine the effluent flowrate using a fluid balance equation that relates the effluent flowrate to a sum between an ultrafiltration removal rate and a total patient fluid input rate that includes the at least one of the dialysis fluid flowrate, the predilution flowrate, or the postdilution flowrate,
        estimate a blood volume using a patient weight,
        determine an adjustment for the IV drug flowrate based on the estimated blood volume of the patient and an amount of the IV drug removed via the determined effluent flowrate,
        determine an adjustment percentage by dividing the adjustment for the IV drug flowrate by the determined effluent flowrate,
        when the adjustment percentage is greater than a threshold, iteratively determine the effluent flowrate and a resulting adjustment for the IV drug flowrate until the adjustment percentage is less than the threshold, and when the adjustment percentage is less than the threshold, implement at least the adjustment for the IV drug flowrate at the infusion pump.

2. The extracorporeal and drug delivery system of claim 1, wherein the renal failure therapy machine is a continuous renal replacement machine, and which includes the effluent pump and at least two of the dialysis fluid pump, the predilution pump, or the postdilution pump.

3. The extracorporeal and drug delivery system of claim 1, wherein the renal failure therapy machine is a hemodialysis machine, and which includes the effluent pump and the dialysis fluid pump.

4. The extracorporeal and drug delivery system of claim 1, wherein the coordinating logic implementor is provided separately from the renal failure therapy machine and the infusion pump, and wherein the coordinating logic implementor is in wired or wireless communication with at least the renal failure therapy machine.

5. The extracorporeal and drug delivery system of claim 4, which is configured such that the total patient fluid input rate is communicated to or determined by the coordinating logic implementor for the coordinating logic implementor to determine the adjustment for the IV drug flowrate.

6. The extracorporeal and drug delivery system of claim 1, which is configured to display the adjustment for the IV drug flowrate at one or more of the renal failure therapy machine, the infusion pump, or the coordinating logic implementor before implementing the adjustment for the IV drug flowrate.

7. The extracorporeal and drug delivery system of claim 1, wherein the coordinating logic implementor is integrated into the renal failure therapy machine.

8. The extracorporeal and drug delivery system of claim 1, wherein the infusion pump is a first infusion pump, the IV drug is a first IV drug, the IV drug flowrate is a first IV drug flowrate, which includes a second infusion pump operable to deliver a second IV drug to the patient at a second IV drug flowrate, and wherein the coordinating logic implementor is configured to determine an adjustment for the second IV drug flowrate based on an amount of the second IV drug removed via the effluent flowrate.

9. The extracorporeal and drug delivery system of claim 1, which is configured such that the determination of the effluent flowrate additionally takes into account the adjustment for the IV drug flowrate.

10. The extracorporeal and drug delivery system of claim 1, which is configured such that the determination of the effluent flowrate additionally takes into account a prescribed patient fluid loss rate.

11. The extracorporeal and drug delivery system of claim 1, wherein the amount of the IV drug removed via the effluent flowrate includes a percentage of the IV drug in the effluent flowrate.

12. The extracorporeal and drug delivery system of claim 1, wherein the threshold is 0.5%.

13. The extracorporeal and drug delivery system of claim 1, wherein the coordinating logic implementor is further configured to take into account blood filter patency or clotting in determining the adjustment for the IV drug flowrate.

14. The extracorporeal and drug delivery system of claim 13, which is configured such that the adjustment for the IV drug flowrate causes the IV drug flowrate to meet a prescribed IV drug flowrate when the amount of the IV drug is removed via the effluent flowrate.

15. The extracorporeal and drug delivery system of claim 1, wherein the renal failure therapy machine is a first renal failure therapy machine, the infusion pump is a first infusion pump, which includes a second renal failure therapy machine associated with a second infusion pump, and wherein the coordinating logic implementor is configured to determine an adjustment for a second IV drug flowrate of the second infusion pump.

16. An extracorporeal and drug delivery system comprising:
a renal failure therapy machine operable with a blood filter in fluid communication with an arterial line for removing blood from a patient to the blood filter and a venous line for returning blood from the blood filter to the patient, the renal failure therapy machine including
an effluent pump positioned and arranged to pump effluent from the blood filter at an effluent flowrate, and
at least one of
a dialysis fluid pump positioned and arranged to pump dialysis fluid to the blood filter at a dialysis fluid flowrate,
a predilution pump positioned and arranged to pump replacement fluid into the arterial line at a predilution flowrate, or
a postdilution pump positioned and arranged to pump replacement fluid into the venous line at a postdilution flowrate;
an infusion pump operable to deliver an intravenous ("IV") drug to the patient; and
a coordinating logic implementor configured to:
determine the effluent flowrate using a fluid balance equation that relates the effluent flowrate to a sum between an ultrafiltration removal rate and a total patient fluid input rate that includes the at least one of the dialysis fluid flowrate, the predilution flowrate, or the postdilution flowrate,
estimate a blood volume using a patient weight,
determine an adjustment to a concentration of the IV drug based on the estimated blood volume of the patient and an amount of the IV drug removed via the determined effluent flowrate,
determine an adjustment value by comparing the adjustment to the concentration of the IV drug to the determined effluent flowrate,
when the adjustment value is greater than a threshold, iteratively determine the effluent flowrate and a resulting adjustment to the concentration of the IV drug until the adjustment value is less than the threshold, and
when the adjustment value is less than the threshold, implement at least the updated effluent flowrate at the effluent pump.

17. The extracorporeal and drug delivery system of claim 16, which is configured to display the adjustment to the concentration of the IV drug at one or more of the renal failure therapy machine, the infusion pump, or the coordinating logic implementor for implementation.

18. The extracorporeal and drug delivery system of claim 16, which is configured such that the adjustment to the concentration of the IV drug causes an IV drug dose received by the patient to meet a prescribed IV drug dose when the amount of the IV drug is removed via the effluent flowrate.

19. The extracorporeal and drug delivery system of claim 16, wherein the infusion pump is a first infusion pump, the IV drug is a first IV drug, which includes a second infusion pump operable to deliver a second IV drug to the patient, and wherein the coordinating logic implementor is configured to determine an adjustment to a concentration of the second IV drug based on an amount of the second IV drug removed via the effluent flowrate.

20. An extracorporeal and drug delivery system comprising:
- a renal failure therapy machine operable with a high flux dialyzer in fluid communication with an arterial line for removing blood from a patient to the high flux dialyzer and a venous line for returning blood from the high flux dialyzer to the patient, the renal failure therapy machine including
  - an effluent pump positioned and arranged to pump effluent from the high flux dialyzer at an effluent flowrate, and
  - at least one of
    - a dialysis fluid pump positioned and arranged to pump dialysis fluid to the high flux dialyzer at a dialysis fluid flowrate,
    - a predilution pump positioned and arranged to pump replacement fluid into the arterial line at a predilution flowrate, or
    - a postdilution pump positioned and arranged to pump replacement fluid into the venous line at a postdilution flowrate;
- an infusion pump operable to deliver an intravenous ("IV") drug to the patient; and
- a coordinating logic implementor configured to
  - determine an adjustment to a flowrate and/or a concentration of the IV drug based on an amount of dilution of the IV drug due to at least one of the dialysis fluid flowrate, the predilution flowrate, or the postdilution flowrate,
  - compare the adjustment to the flowrate and/or the concentration of the IV drug to an adjustment threshold,
  - when the adjustment is greater than the adjustment threshold, iteratively determine the adjustment to the flowrate and/or the concentration of the IV drug until the adjustment is less than the adjustment threshold, and
  - when the adjustment is greater than the adjustment threshold, implement at least the adjustment to the flowrate and/or the concentration of the IV drug at the infusion pump.

21. The extracorporeal and drug delivery system of claim 20, wherein the amount of dilution is based on a relationship between the flowrate of the IV drug, the dialysis fluid flowrate, the predilution flowrate, and the postdilution flowrate.

\* \* \* \* \*